United States Patent [19]

Ishiguro et al.

[11] Patent Number: 5,116,832
[45] Date of Patent: May 26, 1992

[54] PENEM DERIVATIVES PRODUCTION AND USE THEREOF

[75] Inventors: Masaji Ishiguro, Osaka; Hiromitsu Iwata, Takatsuki; Rie Tanaka, Kyoto, all of Japan

[73] Assignee: Suntory Limited, Osaka, Japan

[21] Appl. No.: 652,242

[22] Filed: Feb. 5, 1991

Related U.S. Application Data

[63] Continuation of Ser. No. 135,352, Dec. 21, 1987, abandoned.

[30] Foreign Application Priority Data

Dec. 26, 1986 [JP] Japan .................................. 61-311480

[51] Int. Cl.$^5$ .................. C07D 499/00; A61K 31/425
[52] U.S. Cl. .................................... 514/195; 540/310; 514/192
[58] Field of Search ............... 540/310, 222, 225, 227; 514/192, 195

[56] References Cited

U.S. PATENT DOCUMENTS 4,272,437 6/1981 Menard et al. .................. 260/239 A
4,614,737 9/1986 Hamanaka ......................... 540/310

FOREIGN PATENT DOCUMENTS 61-207387 9/1986 Japan .
2013674A 8/1979 United Kingdom .

*Primary Examiner*—Nicholas S. Rizzo
*Attorney, Agent, or Firm*—Burgess, Ryan & Wayne

[57] ABSTRACT

Novel penem compounds of the formula,

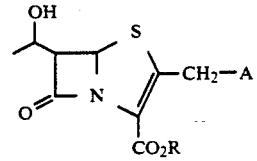

wherein R is hydrogen or allyl, and A is an aliphatic 5- or 6-membered heterocyclic group having one or two oxygens in the ring and their pharmaceutically acceptable salts are produced from the compounds of the formula,

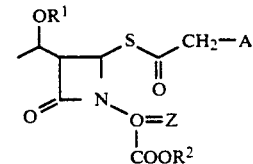

wherein A is the same as above and respective $R^1$ and $R^2$ are protective groups for hydroxyl and carboxyl groups, through several steps. The compounds and their salts are useful as antibacterial agents.

13 Claims, No Drawings

PENEM DERIVATIVES PRODUCTION AND USE THEREOF

This application is a continuation of application Ser. No. 135,352, filed Dec. 21, 1987, now abandoned.

The present invention relates to compounds represented by the general formula:

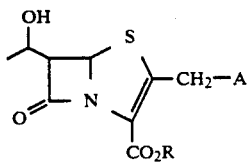

(wherein R denotes hydrogen or allyl group, A denotes an aliphatic 5- or 6-membered heterocyclic group) and pharmcologically acceptable salts thereof.

The present compounds represented by the above general formula (1) are novel and have very remarkable effect in treatment for infections with gram-positive and gram-negative bacteria and can be utilized broadly as medicines for humans as well as animals.

It is well known that many kinds of antibiotics have been invented and employed since the invention of penicillin by Fleming and the employment of penicillin as a chemo-therapeutic agent by Florey.

In the field of antibiotics in Japan, those most widely employed are $\beta$-lactam compounds which account for not less than 80% of all antibiotics employed.

The reasons why the $\beta$-lactam antibiotics are widely employed are the strength of antibacterial activity and the breadth of antibacterial spectrum as well as highly safety of the antibiotics, and a further reason is that they can be obtained by fermentation.

$\beta$-Lactam agents produced by microorganisms, include penicillins, cephalosporins, nocardicins, clavulanic acid, carbapenems etc. Many carbapenem compounds have been already produced by fermenting Actinomycetes or Bacteria, however, penem compounds have an unnatural type of $\beta$-lactam and have not yet been found in natural sources.

The penem skeleton corresponds to that wherein the methylene group at the 1-position of the carbapenem skeleton is replaced by a sulfur atom as shown in the following formula;

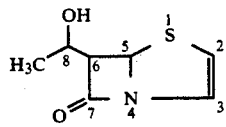

and both skeletons have very analogous structures. The penam skeleton of penicillin causes great strain in the ring. While, the stability of the cephem skeleton in cephalosporins is hindered by the double bond in the six-membered ring so that it reacts with transpeptidase which is relevant to the synthesis of cell wall and inhibits the enzyme's activity. For these reasons, strong activity was expected of the penem skeleton too. In fact, strong activity has been found in 1-thiathienamycin [S.OHYA et al., Antimicrob. Agents Chemother., 21, 492, (1982) and Sch 29482 (A. K. Ganguly et al., J. Antimicrob. Chemother., (Suppl. C) 9, 1 (1982)] etc.

As mentioned in the foregoing, many penem compounds have been synthesized by reasons such as simi-larlity in skeleton with penicillin. For example, there can be exemplified Japanese Patent Application Discosure Nos. 207387/1986, 88291/1979, 25110/1981, 25111/1981 etc.

As to the synthesis of these penem compounds, there have been many reports, for example, A. Longo et al. [Gazz. Chim. Ital., 111, 371-77, (1981)], V. M. Girijavallabhan et al. [Tetrahedron Letters, 22, 3485 (1981)].

Considering to develope new antibiotics, the present inventors took their aim at $\beta$-lactam antibiotics.

Among $\beta$-lactam antibiotics, penem compounds are generally chemically stable and more stable than carbapenem to renal dehydropeptidase I, although there are still many unobvious points in their biological evaluation.

The present inventors have conducted research to find out penem compounds which have, besides the advantages mentioned above, strong activities to the broad range of gram positive and gram-negative bacteria and can be employed even orally, and came to establish the present invention. Furthermore, as a part of the above research, the present inventors have carried out many improvements in the synthesis method to produce penem compounds more cheaply.

The present invention is directed to penem compounds represented by the general formula:

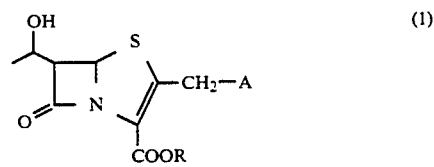

(wherein R denotes hydrogen or allyl group, and A denotes an aliphatic 5- or 6-membered heterocyclic group having one or two oxygen atoms in the ring) and pharmacologically acceptable salts thereof as well as their production method and use for antibiotics.

The penem compounds represented by the above general formula (1) can be synthesized by the following methods.

Firstly, there is described a production method of azetidinone compounds (2) which are the precursors for producing the penem compounds.

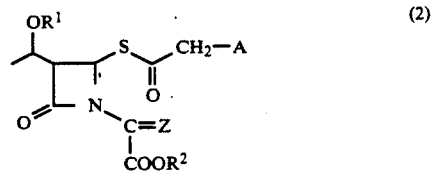

(wherein $R^1$ denotes a protective group for hydroxyl group, $R^2$ denotes allyl or a protective group for carboxyl group, A has the same definition as above, and Z denotes oxygen atom, a triarylphosphonio group or a trialkylphosphonio group). The compounds of the general formula (2) can be derived from the known compounds of the general formula (2'),

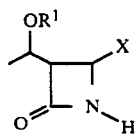

(wherein $R^1$ has the same definition as above and X denotes a hlogen atom, acetoxy group, arylsulphonyl group or alkylsulphonyl group). The compounds (2') are described, for instance, in Japanese Patent Application Disclosure No. 207373/1986.

There are two isomers in the azetidinone derivatives of the general formula (2). The isomers are 1'R,3S,4R, compound (2a) and 1'R,3R,4S compound (2b).

(2a)

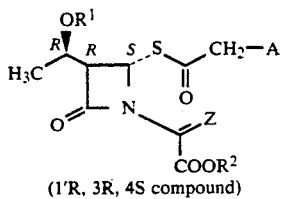

(1'R, 3R, 4S compound)

(wherein $R^1$, $R^2$, A and Z have the same definitions as above).

The former isomer has the same steric configuration as thienamycin. The separation of two isomers can be carried out very easily by recrystallization.

The azetidinone derivatives having the general formula (2) can be produced, for example, by the method illustrated in the following:

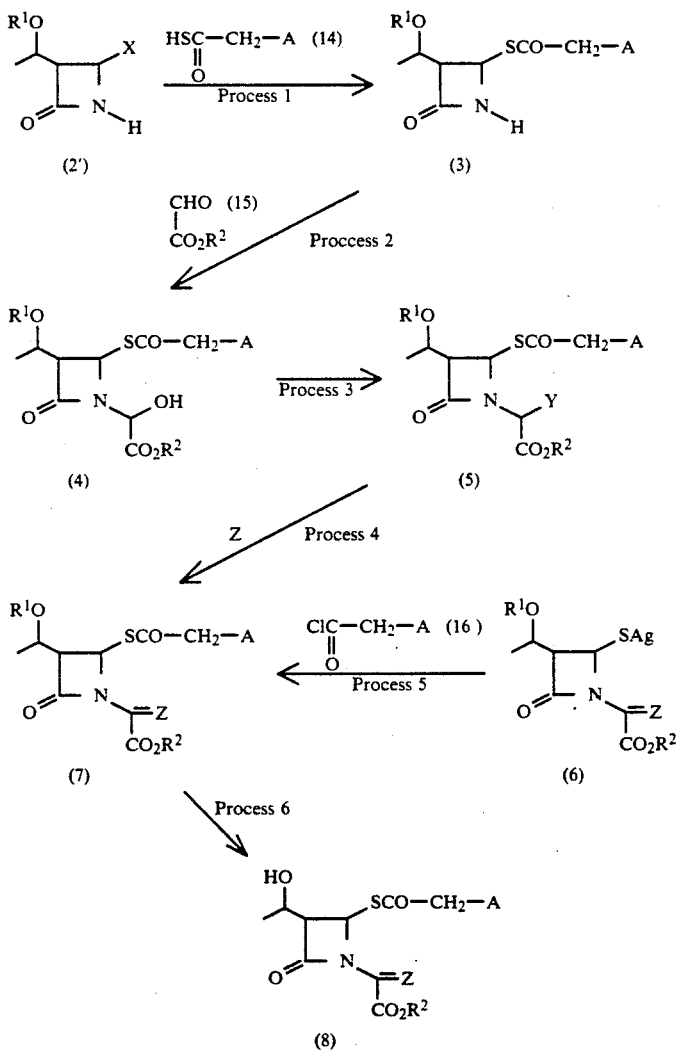

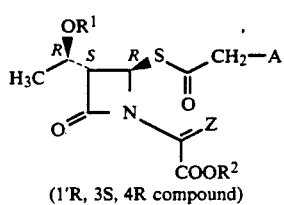

(1'R, 3S, 4R compound)

(wherein $R^1$, $R^2$, Z, X, R and A have the same definitions as above, and Y denotes a hologen atom such as chlorine, bromine etc.).

Concrete structures of the group denoted by the symbol A are exemplified as follows:

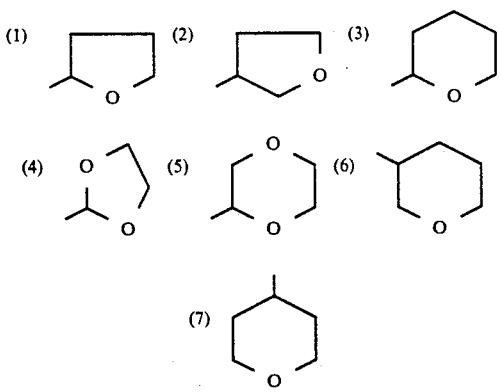

In the compounds represented by the above-mentioned general formula (1), there are optical and steric isomers owing to the asymmetric carbons, though all of them are shown by a plane formula, and the scope of the present invention is not limited by the plane formula. However, a compound wherein the carbon atom at 5-position of the penem skeleton has R configuration and the carbon atom at 6-position has S configuration can be selected. With regard to 1-hydroxyethyl group, a substituent at 6-position, R configuration is preferable. With regard to the carbon atom at 2-, 3- or 4-position of the group A, R configuration is preferable in some cases, which is the same as already reported by the present inventors (Japanese Patent Application Disclosure No. 207373/1986. However, the present compounds have, as the case may be, similar effects in both R and S configurations, therefore, the configuration of the carbon atom is not particularly limited and the mixture of both configurations may be employed. This is one of the features of the present invention.

Process 1 is that of obtaining a thiocarboxylic acid ester of the general formula (3), wherein an azetidinone derivative of the general formula (2) is condensed with 1 to 2 equivalents of a thiocarbonic acid of the general formula (14) under the presence of a suitable base. As the base, an alkali metal hydroxide such as sodium hydroxide, potassium hydroxide etc., an alkali metal carbonate such as sodium hydrogencarbonate, potassium hydrogencarbonate etc., or an alkali metal alcoholate such as sodium methylate, sodium ethylate is preferable. The reaction is carried out in a liquid medium, for example, water and an alcohol such as methanol, ethanol etc., a ketone such as acetone, methyl ethyl ketone etc. or an ether such as tetrahydrofuran, dioxane etc. or a halogenated hydrocarbon such as methylene chloride, chloroform etc. The reaction can be performed at a pH from 8 to 12. After the reaction is finished, the mixture is extracted with a water-immiscible solvent, followed by washing the organic layer with water.

After the organic layer is dried with a drying agent, organic solvent in the layer is distilled off to obtain the compound (3).

In this reaction, the compound (3) can be obtained also by employing, as the base, an organic amine such as triethylamine, pyridine, lutidine etc., a metal hydride such as lithium hydride, sodium hydride etc., or a metal carbonate such as sodium hydrogencarbonate, potassium hydrogencarbonate etc., employing, as the solvent, an alcohol such as methanol, ethanol etc., a halogenated hydrocarbon such as methylene chloride, chloroform etc., a hydrocarbon such as benzene, toluene etc., an ether such as ether, tetrahydrofuran etc., a ketone such as acetone, methyl ethyl ketone etc., or nitromethane, dimethoxyethane, acetonitrile etc., and sirring the mixture in the absence of water at 30° C. to 80° C.

The products of this reaction may be employed in the next process without purification, however, the products can be purified further by column chromatography, preparative thin layer chromatography, recrystallization etc.

Process 2 is that of producing a N-hydroxyl ester compound of the general formula (4) by heating and refluxing a compound of the general formula (3) with a glyoxylic acid ester of the general formula (15) in a solvent, for example, an ether such as tetrahydrofuran, dioxane etc. or an aromatic hydrocarbon such as benzene, toluene, and xylene etc. or a halogenated hydrocarbon such as methylene chloride, chloroform etc. In this reaction, there may be added a base such as trimethylamine, 2,6-lutidine to the mixture. The product of this process can obtained by distilling off the solvent from the reaction mixture, and, in many cases, can be employed without further purification in the next process. However, as the case may be, it can be purified by column chromatography, recrystallization etc.

Process 3 is that of producing a compound of the general formula (5). The reaction of this process can be performed by dissolving a compound of the general formula (4) into a halogenated hydrocarbon such as methylene chloride, chloroform etc., an aromatic hydrocarbon such as benzene toluene etc. or an ether such as ether, tetrahydrofuran etc. and contacting with a thionyl halide such as thionyl chloride, thionyl bromide etc., a phosphorus halide such as phosphorus pentachloride etc., a phosphorus oxyhalide such as phosphorus oxychloride etc. or a methanesulfonyl halide such as methanesulfonyl bromide etc. in the presence of a base such as triethylamine, pyridine, 2,6-lutidine, diisopropylethylamine etc. This reaction can be performed at a temperature of $-40°$ C. to $0°$ C. and finished within several hours in many cases.

The product of this process can be available by diluting the reaction mixture with a water-immiscible solvent, washing the solution with a saturated aqueous solution of sodium hydrogencarbonate and then water, drying the washed solution by the addition of a drying agent, and removing the solvent by distillation. The product thus obtained can be employed without further purification in the next process. However, it may be purified by a procedure such as column chromatography. In many cases, a crude porduct simply obtained by filtering the reaction mixture to remove insoluble materials and concentrating the filtrate can be employed in the next process.

Process 4 is that of producing a phosphoranilidene compound of the general formula (7). In carrying out the reaction of this process, the compound of the general formula (6) is mixed with an organic solvent, and after adding thereto triarylphosphine such as triphenylphosphine etc. or trialkylphosphite such as triethylphosphite, the mixture is heat-treated in the presence of a base. Prefered reaction temperature is room temperature to 100° C. As the base usually employed, there may be exemplified triethylamine, diisopropylethylamine, pyridine, 2,6-lutidine etc.

As the solvent, an ether such as tetrahydrofuran, dioxane etc., an aromatic hydrocarbon such as benzene, toluene, xylene etc. or an aliphatic hydrocarbon such as hexane, cyclohexan etc. is preferable.

After the reaction is finished, insoluble materials are filtered off from the reaction mixture, the filtrate is washed with dilute acid, dilute alkali and water in the order, dried with a drying agent and concentrated to obtain the product compound (7). The product (7) may be purified by a procedure such as column chromatography, preparative thin layer chromatography, recryctallization etc., if necessary.

Process 5 is that for condensing a known compound (Japanese Patent Application Disclosure No. 25110/1981) of the general formula (6) with an acid chloride of the general formula (16) (wherein group A has the same definition as previously described) to obtain the same product compound as that of Process 4.

The reaction of this process is performed by diluting a compound of the general formula (6) with a solvent, for example, a halogenated hydrocarbon such as methylene chloride, chloroform etc., an aromatic hydrocarbon such as benzene, toluene, xylene etc. or an ether such as ether, tetrahydrofuran etc. and adding thereto an acid chloride of the general formula (16) dissolved in the same solvent as employed in the above dilution. The reaction can be carried out at a temperature from 0° C. to room temperature and finished within several hours. After the reaction is finished, insoluble materials in the reaction mixture are removed by filtration. The filtrate is washed with water, dried with a drying agent and concentrated, whereby the product compound (7) is obtained. This product can be employed without purification in the next process, however, it can be purified by a procedure such as column chromatography, recrystallization etc. Before explaining Process 6, the production processes from the above-mentioned compounds (7) and (8) to present penem derivatives (1) are illustrated as follows:

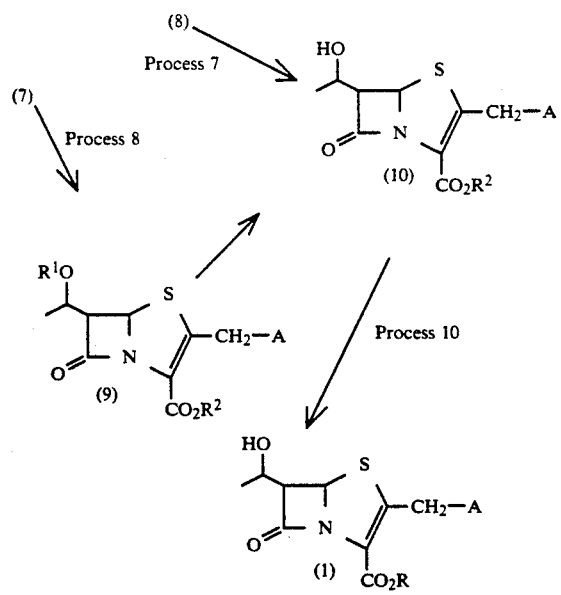

(wherein $R^1$, $R^2$, R and A have the same definitions as above)

Process 6 is that of obtaining a compound of the general formula (8) by removing a protective group for hydroxyl group of the compound of the general formula (7). The subsequent Process (7) is that of obtaining a penem compound of the general formula (10) by cyclizing a compound of the general formula (8). These successive two processes can be operated by the same manner in reverse order to obtain a penem compound of the general formula (10). Namely, the penem compound (10) can be obtained by cyclizing the compound of the general formula (7) in Process 8, and then removing the protective group in Process 9.

Process 6 or 9 is that of removing a protective group for hydroxyl group of a penem compound (7) or (9). The procedure for removing the protective group varies depending of the property of each protective group. For example, in case that the protective group is a silyl group such as tert-butyldimethylsilyl etc., the compound of the formula (7) or (9) is diluted with a solvent and contacted with tetrabutylammonium fluoride, whereby the reaction is performed easily. The reaction temperature may be in the neighborfood of room temperature. Preferred sovent is an ether such as dioxane, tetrahydrofuran etc.

After the reaction is finished, the reaction mixture is diluted with a water-immiscible solvent, washed with diluted alkali and water in order, dried with a drying agent and concentrated, whereby the compound (8) is obtained from the compound (7) or the compound (10) from the compound (9). The product can be employed without putification in the next process, however, it can be purified by a procedure such as column chromatography, preparative thin layer chromatography, recrystallization etc.

Process 7 or 8 is that of subjecting a compound of (8) or (7) to heat-cyclization to produce a penem compound having the structure of the general formula (10) or (9).

In carrying out this process, a solvent employed in the reaction is not limited particularly, and an aromatic hydrocarbon such as benzene, toluene, xylene etc. and an ether such as dioxane, diethoxyethane etc. are preferable.

After the reaction is finished, the product compound of the process can be obtained by distilling off the solvent from the reaction mixture.

The compound (10) and (9) thus obtained can further be purified by a procedure such as column chromatograpy, preparative thin layer chromatography, recrystallization etc., if necessary.

Process 10 is that of producing a penem compound of the general formula (1), wherein the protective group for carboxyl group in the penem derivative of the general formula (10) is removed.

The procedure for removing the protective group varies depending of the kind of the group and it can be removed, in general, by a procedure known in the art of this field.

For example, in case that the protective group is an aralkyl group such as benzyl or p-nitrobenzyl, there may be exemplified procedures reacting hydrogen and a catalyst for hydrogenolysis such as palladium-carbon, or reacting an alkali metal sulfide such as sodium sulfide, with the penem derivative.

In case that the protective group is allyl, there may be exemplified a procedure employing triarylphosphine and tetrakis(triarylphophine)palladium, and also a procedure employing tetrakis(triarylphosphine)palladium, tri-n-butyltin hydride and acetic acid.

In case that the protective group is α,α,α-trichloroethyl group, there may be exemplified a procedure reacting zinc with the penem derivative at pH 3 to 7.

The reaction is carried out in the presence of a solvent which is not limited particularly, as far as it is unrelevant to the reaction.

In case that an aralkyl group or α,α,α-trichloroethyl group is employed as the protective group, preferred solvents are an alcohol such as methanol, ethanol etc., an ether such as ether, tetrahydrofuran etc., an ester such as methyl acetate, ethyl acetate, an aliphatic acid such as acetic acid etc., and a mixture of the above sovent(s) and water. As the case may be, the reaction is accelerated by adjusting the pH of the reaction mixture to a suitable value of 3 to 8.

In case that the protective group is allyl group, preferred solvents are an ether such as ether, tetrahydrofuran etc. or and ester such as methyl acetate, ethyl acetate etc., and the reaction is usually carried out in the absence of water.

In case that the protective group is an aralkyl or allyl group, the reaction mixture is adjusted to weak alkaline after the reaction is finished, resulting organic layer is removed and the aqueous layer is concentrated, whereby the product compounds (1) are obtained as their salts. In case that the protective group is allyl group, the salts of the product compounds (1) are also obtained as crystals which can be deposited by adding an alkali metal salt of an aliphatic acid such as sodium 2-ethylhexanoate, potassium 2-ethylhxanoate etc. directly to the reaction mixture.

In case that the protective group is ααα-trichloroethyl group, the reacition is carried out under acidic condition. After the reaction is finished, organic layer in the mixture is separated, washed with water, dried with a drying agent and concentrated, whereby the product compounds (1) can be obtained as free acids.

The salts of the compounds (1) obtained by the foregoing procedures can be converted to the free acids by treating the salt with a suitable acid. Reversely, it is apparent that the free acids of compounds (1) obtained by the procedures mentioned later can be converted to the salts by contacting with an alkali metal carbonate such as sodium hydrogencarbonate, potassium hydrogencarbonate or an alkali metal salt of an aliphatic acid such as sodium 2-ethylhexanoate, potassium 2-ethylhexanoate etc. It is advantageous that these conversions are easily carried out because present compounds are relatively stable against acids or bases.

The product compounds (1) can further be purified, if necessary, by a procedure such as column chromatography, preparative thin layer chromatography, recrystallization etc.

The intermediate compound (9) obtained by the foregoing synthetic route can also be produced by applying other known synthetic method [e.g. A. Afonso et al., J. Am. Chem. Soc., 104, p. 6138 (1982); A. Yoshida et al., Chem. Pharm. Bull., 31, p. 768 (1983)].

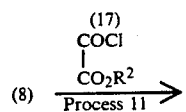

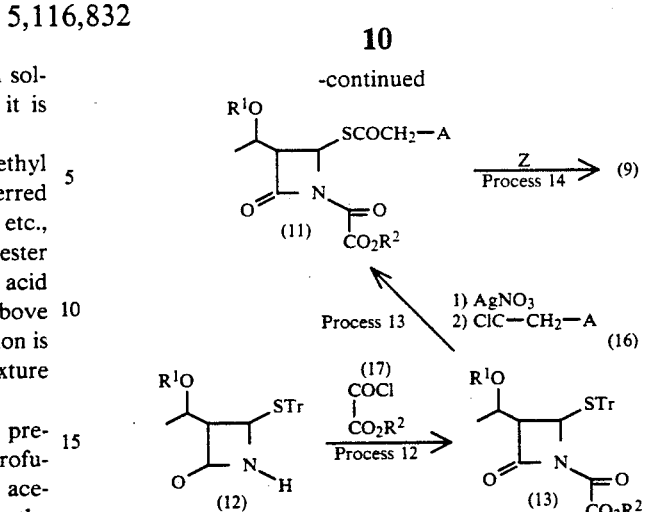

(wherein $R^1$, $R^2$, Z and A have the same definitions as above; Tr denotes triphenylmethyl group).

Hereinafter, the above-illustrated processes are explained in order.

In the first place, Process 11 is that of obtaining a compound of the general formula (11) by condensing a compound of the general formula (3) previously described with an oxalyl chloride monoester of the general formula (17). This process can be carried out by diluting the compound (3) with a solvent and dropping thereto the compound (17) diluted with a solvent in the presence of a suitable base.

Preferred reaction temperature is −40° C. to 20° C. As the base, an alkali metal hydride such as sodium hydride, lithium hydride etc., an alkali metal alcoholate such as sodium methylate, sodium ethylate etc., an aliphatic amine such as triethylamine, diisopropylethylamine etc. may be employed and an aromatic amine such as pyridine, 2,6 lutidine etc. are preferable. The solvent is not limited particularly, so far as it is unrelevant to the reaction, and preferred solvents are an ether such as tetrahydrofuran, dioxane etc., a halogenated hydrocarbon such as methylene chloride, chloroform etc., and an aromatic hydrocarbon such as benzene, toluene, zylene etc.

After the reaction is finished, insoluble materials are filtered off from the reaction mixture and the solvent is distilled off from the filtrate, whereby product compounds can be obtained. As the case may be, the filtrate obtained by filtering off the insoluble materials is washed with diluted alkali and water in order, dried with a drying agent and concentrated, whereby the products (11) are also obtained.

The conmpound (11) thus obtained can be employed in the next process without purification, however, it can be purified by column chromatography utilizing silica gel having decreased activity etc.

The compounds obtained in this process can also be obtainaed by the continuous procedure of Processes 12 and 13 as described in the following:

Firstly, Process 12 is that of obtaining a compound of the general foramula (13) by condensing a known compound of the general formula (12) (cf. Japanese Patent Application Disclosure No. 25110/1981) with an oxalyl chloride monoester of the general formula (17). This process can be carried out in the same manner as Process 11.

Secondary, Process 13 is that of converting the compound (13) to a compound of the general formula (11), wherein the compound (13) obtained in Process 12 is converted temporarily to a silver mercaptide compound which is immediately condensed with an acid chloride of the general formula (16).

In carrying out this process, the compound (13) is diluted with an organic solvent, added thereto silver nitrate dissolved in the same solvent as above in the presence of a suitable base, and the mixture is stirred preferably at $-10°$ C. to $10°$ C. In the mixture, there is formed silver mercaptide, an intermediate, which is not isolated, and the acid chloride (16) diluted with a suitable solvent is added thereto and stirred preferably at $110°$ C. to room temperature, whereby the product compound (11) is obtained.

The solvent employed in the reaction is rquired to dissolve silver nitrate and not to be relevant to the reaction. Preferable solvent is an ether such as tetrahydrofuran, dimethoxyethane etc., nitromethane or actonitrile.

As the base, an aliphatic amine such as triethylamine, diisopropylamine etc., an aromatic amine such as pyridine, 2,6-lutidine etc., and a diamine such as 1,5-diazabicyclo[4,3,0]-5-ene, 1,8-diazabicyclo[5,4,0]undece-7-ene etc.

For diluting the acid chloride, a solvent unrelevant to the reaction may be emloyed. Preferable sovents are those employed in the above reaction, namely, the ethers exemplified as above, nitromethane, acetonitrile etc. A halogenated hydrocarbon such as methylene chloride, chloroform etc. and an aromatic hydrocarbon such as benzene, toluene etc. are also preferable.

The product of this process is the same as that of Process 11 and, after the reaction is finished, it can be obtained by the same manner as in Process 11.

The compound (11) produced by this process, similarly to the compound (11) obtained by Process (11), can be employed without purification, in many cases, in the next process. However, it can be purified by a procedure such as column chromatography etc.

The compound (11) thus obtained is derived to a previously-mentioned penem compound of the general formula (9) in the next Process 14.

The compound (11) is mixed with a triarylphosphine such as triphenylphosphine etc. or a trialkylphosphite such as triethylphosphite, trimethylphosphite etc. and then the mixture is diluted with solvent and stirred at room temperature to $140°$ C., whereby the product compound (9) can be obtained. As the solvent, a halogenated hydrocarbon such as methylene chloride, chloroform etc., an ether such as tetrahydrofuran, dioxne etc., an aromatic hydrocarbon such as benzene, toluene, xylene etc. and an aliphatic hydrocarbon such as hexane, cyclohexane etc. are preferable. Depending on the case, an antioxidant such as hydroquinone may be added to the reaction mixture.

The product compound (9) obtained in this reaction is the same as the product obtained in Process 8 and can be purified in the same manner as in Process 8.

Recently, intensive studies are proceeding in the field of the present invention and there have been published many reports concerning production methods for penem comopounds.

Therefore, it is reasonable to presume that present compound can be produced by applying one of these methods and the production of present compounds is not limited to the methods explained herein.

In the above-mentioned method of producing present compounds, there is no reference to stereochemistry, however, it is natural that the method is applicable in the same manner to a synthesis employing the corresponding optical active compound.

Particularly, present compounds have the following features:

In case that any one of the lactam compounds of the general formula (2), the thiocarbonic acid compounds of the general formula (14) and the acid chloride compounds of the general formula (16) is an optical active compound, even if the other compound to be reacted with it is a dl-compound, an optical active compound can be obtained, because optical resolution is carried out in purifying the product of Process 1, 8, 9 or 14.

Preferable means for the optical resolutin is recrystallization, column chromatography or preparative thin layer chromatography.

A present compound of the general formula (1) wherein R is hydrogen can be converted to a pharmaceutically acceptable salt, if necessary. As the salt, there may be exemplified a metal salt such as lithium, sodium, potassium, calcium or magnesium salt, an amino acid salt such as lysine salt etc., or ammonium salt. Sodium or Potassium salt is preferable.

Although present penem compounds of the general formula (1) exhibit strong antibacterial activity in the form of a racemate, there may be exemplified as the most desirable form in the isomers, a compound which has (5R,6S) configuration and, with regard to 1-hydroxyethyl group, the substituent at 6-position, has R configuration.

The present compounds are novel and have strong antibacterial activity. This is clear from a comparison of antibacterial activity in vitro with other compounds which were synthesized separately by present inventors.

The present compounds have antibacterial activity which can be determined by standardized dilution assay method in vitro.

By employing such standardized microbiological method, it was found that present compounds show acivities in a test amount of 0.025 to 12.5 $\mu$g/ml against gram-positive bacteria such as *Staphylococcus aureus, Micrococcus luteus*, etc.; gram-negative bacteria such as *Eschrichia coli, Klebsiella pneumonia, Serratia marcescens, Proteus morganii, Enterobactor colacea, Alkaligenes faecalis* etc.; *Proteus vulqaris;* anaerobic bacteria such as *Bacterioides fragilis* and *Fusobacterium varium.*

The present compounds of the general formula (1) are markedly stable against renal dehydropeptidase, show low toxicity values ($LD_{50}$) in vivo similar to general penem compounds and can be prescribed for oral, parenteral and external administration.

Although the dose of the present compounds depends on many factors, a typical daily dose for an adult is 50 mg to 5 g and may be preferably administered dividedly in a daily amount of 100 mg to 4 g. In general, it may be administered as a dose unit containing a suitable amount of the active ingredient and a biologically acceptable carrier or diluent.

For oral administration there may be employed tablets or capsules which contain the active ingredient as well as a diluent, for example, lactose, glucose, sucrose, mannitol, sorbitol or cellulose, and a lubricant such as talc, stearic acid or its salt. The tablets may further contain a binder, for example, magnesium silicate, starch etc.

For parenteral administration, it is suitable to employ an isotonic aqueous solutin or an emulsion.

The present compounds may be employed not only for human use but for animal use too.

The protective group employed in the synthesis of the present compounds may be any protective group usually employed in the field of β-lactam compounds.

As a suitable protective group for the hydroxyl group, there may be exemplified t-butyldimethylsilyl group, t butoxycarbonyl group, p nitrobenzyloxycarbonyl group, 2,2,2, trichloroethoxycarbonyl group etc.

As a protective group for the carboxyl group, there may be exemplified allyl group, 2,2,2-trichloroethyl group, t-butyl group, p-nitrobenzyl group etc., and allyl group is preferable.

In the following formulation examples, the active ingredient may be, for example, sodium (5R,6S) 6 (1(R)-hydroxyethyl)-2-(3-tetrahydrofuranyl)methylpenem 3-carbonate or an equivalent amount of any other present compound.

FORMULATION EXAMPLE 1

| No. | (Capsules) Ingredients | mg/capsule | mg/capsule |
|---|---|---|---|
| 1 | Active ingredient | 250 | 100 |
| 2 | Corn starch | 20 | 10 |
| 3 | Magnesium stearate | 5 | 2 |
|   | Total amount | 275 | 112 |

Procedure

The ingredients 1 and 2 were mixed in a suitable mixing machine, the ingredient 3 was added thereto and the mixture was further mixed. The mixed ingredients were filled into capsules employing a capsule-filling machine.

FORMULATION EXAMPLE 2

| No. | (Tablets) Ingredients | mg/tablet |
|---|---|---|
| 1 | Active ingredient | 250 |
| 2 | Lactose | 55 |
| 3 | Corn starch | 40 |
| 4 | Magnesium stearate | 5 |
|   | Total amount | 350 |

Procedure

The ingredients 1 to 3 were mixed in a suitable mixing machine and the ingredient 4 was added thereto and mixed for further several minutes. The mixture was compressed with a suitable tableting machine to a prescribed size and weight.

FORMULATION EXAMPLE 3

| Ingredient | (Ampoules) Amount (g) in a ampoule | | |
|---|---|---|---|
| Active ingredient | 1.0 g | 0.5 g | 0.25 g |

Procedure

A sterilized aqueous solution of active ingredient was filled into an ampoule of 20 ml, 10 ml or 5 ml so as to make each ampoule contain 1.0 g, 0.5 g or 0.25 g of the active ingredient and sealed.

REFERENCE EXAMPLE 1

(3S,4R)-1-(1-Allyloxycarbonyl-2-triphenylphosphoranylidenemethyl)-3-[1(R)-tert-butyldimethylsilyloxyethyl-2-oxo-4-[(2-tetrahydrofuranyl)methylcarbonylthioazetidine (2)

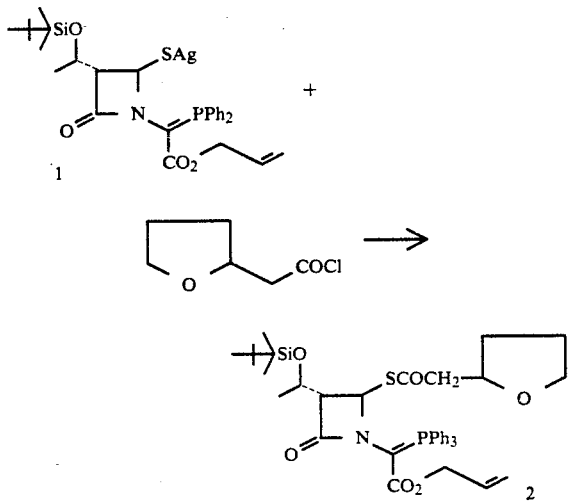

In methylene chloride (7 ml) was dissolved (3S,4R)-1-(1-allyloxycarbonyl-2-triphenylphosphoranylidenemethyl)-3-[(R)-1-tert-butyldimethylsilyloxyethyl]-2 oxo-4-silver-thioazetidine (1) (0.97 g), and a mixture of tetrahydrofuran- 2-acetyl chloride (0.223 g) and methylene chloride (1 ml) was added dropwise to the solution under stirring at 0° C. After stirring for 90 minutes at the same temperature, the insoluble matter was filtered out, and the filtrate was washed with saturated aqueous sodium hydrogencarbonate solution and water, successively, and then dried over anhydrous sodium sulfate. The solvent was removed by distillation, and the resulting residue was purified by column chromatography to give 0.596 g of the subject compound (2) in the form of a colorless amorphous substance.

REFERENCE EXAMPLE 2

(3S,4R)-1-(1-allyloxycarbonyl-2-triphenylphosphoranylidenemethyl)-3-[1(R)-tert-butyldimethylsilyloxyethyl]-2-oxo-4-{[2(R)-tetrahydrofuranyl]-methylcarbonylthio}azetidine (3)

Silver-mercaptide compound (1) (1.88 g) and (R)-tetrahydrofuran-2-acetyl chloride (0.46 g) were treated by the same procedure as described in Reference Example 1 to give 0.83 g of the subject compound (3) in the form of a yellowish oily substance.

REFERENCE EXAMPLE 3

(3S,4R)-1-(1-allyloxycarbonyl-2-triphenylphosphoranylidenemthyl)-2-[1(R)-tert-butyldimethylsilyloxyethyl]-2-oxo-4-[(3-tetrahydrofuranyl)methylcarbonylthio]azetidine (4)

Silver-mercaptide compound (1) (1.88 g) and tetrahydrofuran-3-acetyl chloride (0.46 g) were treated by the same procedure as described in Reference Example 1 to give 0.738 g of the subject compound (4) in the form of a colorless amorphous substance.

REFERENCE EXAMPLE 4

(3S,4R)-1-(1-allyloxycarbonyl-2-triphenylphosphoranylidenemethyl)-3-[1(R)-tert-butyldimethylsilyloxyethyl-]-2-oxo-4-[(2-tetrahydropyranyl)methylcarbonylthio]azetidine (5)

Silver-mercaptide compound (1) (1.453 g) and tetrahydropyranylacetyl chloride (0.325 g) were treated by the same procedure as described in Reference Example 1 to give 0.354 g of the subject compound (5) in the form of a yellow oily substance.

REFERENCE EXAMPLE 5

(3S,4R)-1-(1-Allyloxycarbonyl-2-triphenylphosphoranylidenemethyl)-3-[1(R)-tert-butyldimethylsilyloxyethyl]-4-[(1,3-dioxolane-2-yl)methylcarbonylthio]-2-oxoazetidine (6)

Silver mercaptide compound (1) (1.71 g) and (1,3-dioxolane-2-yl)acetyl chloride (0.80 g) were treated by the same procedure as described in Reference Example 1 to give 0.32 g of the subject compound (6) in the form of a yellowish oily substance.

REFERENCE EXAMPLE 6

(3S,4R)-1-(1-Allyloxycarbonyl-2-triphenylphosphoranylidenemethyl)-3-[1(R)-tert-butyldimethylsilyloxyethyl]-4-[(1,4-dioxane-2-yl)methylcarbonylthio]-2-oxoazetidine (7)

Silver mercaptide compound (1) (1.453 g) and (1,4-dioxane-2-yl)acetyl chloride (0.329 g) were treated by the same procedure as described in Reference Example 1 to give 0.432 g of the subject compound (7) in the form of a yellow oily substance.

REFERENCE EXAMPLE 7

Allyl (5R,6S)-6-[1(R)-tert-butyldimethylsilyloxyethyl]-2-(2-tetrahydrofuranyl)methylpenem-3-carboxylate (8)

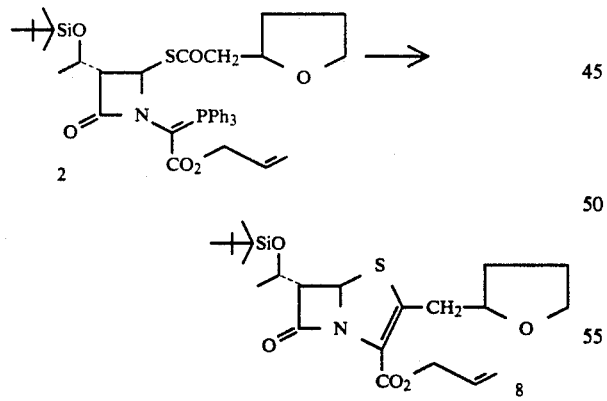

A mixture of (3S,4R)-1-(1-allyloxycarbonyl-2-triphenylphosphoranylidenemethyl)-3-[1(R)-tert-butyldimethylsilyloxyethyl]-2-oxo-4-[(2-tetrahydrofuranyl)methylcarbonylthio]azetidine (2) (550 mg, 0.75 mmole) and toluene (55 ml) was stirred at 120° C. for 7 hours. After cooling, the mixture was concentrated under reduced pressure, and the residue was purified by silica gel column chromatography to give 306 mg (90%) of the subject compound in the form of a colorless solid substance.

REFERENCE EXAMPLE 8

Allyl (5R,6S)-6-[1(R)-tert-butyldimethylsilyloxyethyl]-2-[2(R)-tetrahydrofuranyl]methylpenem-3-carboxylate (9)

(3S,4R)-1-(1-Allyloxycarbonyl-2-triphenylphosphoranylidenemethyl)-3-[1(R)-tert-butyldimethylsilyloxyethyl]-2-oxo-4-{[2(R)-tetrahydrofuranyl]methylcarbonylthio}azetidine (3) (806 mg, 1.1 mmole) and toluene (81 ml) were treated by the same procedure as described in Reference Example 7 to give 346 mg (69 %) of the subject compound (9) in the form of a colorless solid substance.

REFERENCE EXAMPLE 9

Allyl (5R,6S)-6-[1(R)-tert-butyldimethylsilyloxyethyl]-2-(3-tetrahydrofuranyl)methylpenem-3-carboxylate (10)

(3S,4R)-1-(1-Allyloxycarbonyl-2-triphenylphosphoranylidenemethyl)-3-[1(R)-tert-butyldimethylsilyloxyethyl]-2-oxo-4-[(3-tetrahydrofuranyl)methylcarbonylthio]azetidine (4) (704 mg, 0.96 mmole) and toluene (70 ml) were treated by the same procedure as described in Reference Example 7 to give 302 mg of the subject compound (10) in the form of a colorless solid substance.

REFERENCE EXAMPLE 10

Allyl (5R,6S)-6-[1(R)-tert-butyldimethylsilyloxyethyl]-2-(2-tetrahydropyranyl)methylpenem-3-carboxylate (11)

(3S,4R)-1-(1-Allyloxycarbonyl-2-triphenylphosphoranylidenemethyl)-3-[1(R)-tert-butyldimethylsilyloxyethyl]-2-oxo-4-[(2-tetrahydropyranyl)methylcarbonylthio]azetidine (5) (354 mg, 0.47 mmole) and toluene (30 ml) were treated by the same procedure as described in Reference Example 7 to give 124 mg (56%) of the subject compound (11) in the form of a yellow oily substance.

REFERENCE EXAMPLE 11

Allyl (5R,6S)-6-[1(R)-tert-butyldiemthylsilyloxyethyl]-2-(1,3-dioxolane-2-yl)methylpenem-3-carboxylate (12)

(3S,4R)-1-(1-Allyloxycarbonyl-2-triphenylphosphoranylidenemethyl)-3-[1(R)-tert-butyldimethylsilyloxyethyl)methylcarbonylthio]-2-oxoazetidine (6) (309 mg, 0.42 mmole) and toluene (30 ml) were treated by the same procedure as described in Reference Example 7 to give 150 mg (79 %) of the subject compound (12) in the form of a colorless solid substance.

REFERENCE EXAMPLE 12

Allyl (5R,6S)-6-[1(R)-tert-butyldimethylsilyloxyethyl]-2-(1,4-dioxane-2-yl)methylpenem-3-carboxylate (13)

(3S,4R)-1-(1-Allyloxycarbonyl-2-triphenylphosphoranylidenemethyl)-3-[1(R)-tert-butyldimethylsilyloxyentyl]- 4-[(1,4-dioxane-2-yl)methylcarbonylthio]-2-oxoazetidine (7) (432 mg, 0.577 -mole) and toluene (30 ml) were treated by the same procedure as described in Reference Example 7 to give 87 mg (32 %) of the subject compound (13) in the form of a yellow oily substance.

REFERENCE EXAMPLE 13

Allyl (5R,6S)-6-[1(R)-tert-butyldimethylsilyloxyethyl]-2-(2-tetrahydrofuranyl)methylpenem-3-carboxylate (8)

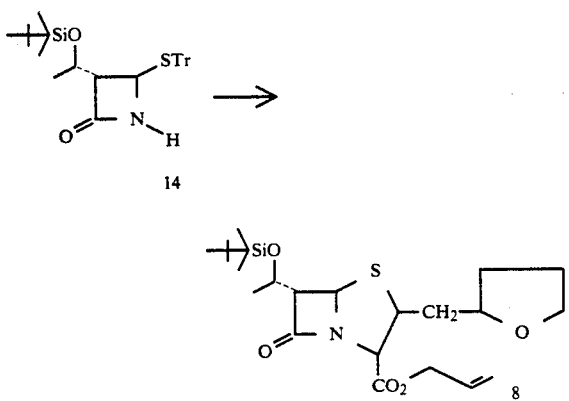

(1) In methylene chloride (16 ml) was dissolved (3S,4R)-3-[1(R)-tert-butyldimethylsilyloxyethyl]-2-oxo-4-triphenylmethylthioazetidine (14) (2.02 g, 4 mmole), and diisopropylethylamine (2.26 g, 18 mmole) was added to the solution under stirring at 0° C., followed by addition of a mixture of allyloxalyl chloride (2.61 g, 18 mmole) and methylene chloride (16 ml) at the same temperature. After stirring for 25 minutes, the reaction mixture was washed with 5% aqueous potassium hydrogensulfate solution, saturated sodium hydrogencarbonate solution and water, successively, and dried over anhydrous sodium sulfate. The solvent was removed under reduced pressure to give (3S,4R)-1-allyloxyoxalyl-3-[1(R)-tert-butyldimethylsilyloxyethyl]-2-oxo-4-triphenylmethylthioazetidine in the form of a brown oily substance. The compound was used in the subsequnet reaction without being purified.

(2) The above-described crude compound was dissolved in acetonitrile (8 ml), and a mixture of pyridine (0.32 g) and acetonitrile (4 ml) was added to the solution under stirring at 0° C., followed by addition of a solution of silver nitrate 91.08 g) in acetonitrile (8 ml) at the same temperature. The mixture was stirred for 2 hours at at 0° C. and admixed with tetrahydrofuranylacetyl chloride (0.95 g, 6.2 mmole) at the same temperature, followed by stirring for further 25 minutes. The insoluble matter was filtered out, and the filtrate was diluted with ethyl acetate (50 ml), which was then washed with saturated aqueous sodium hydrogencarbonate solution and 5% aqueous potassium hydrogensulfate solution, successively. The solution was dried over anhydrous sodium sulfate, and the solvent was removed by distillation under reduced pressure to give (3S,4R)-1-allyloxooxalyl 3-[1(R)-tert-butyldimethylsilyloxyethyl]-2-oxo-4-[(2-tetrahydrofuranyl)methylcarbonylthio]azetidine in the form of a brown oily substance. The compound was used in the next reaction without being purified. (3) A mixture consisting of the above-described crude product, xylene (17.6 ml) and triethylphosphite (3.6 ml) was stirred at 130 to 140° C. for 3 hours, and after cooling, the mixture was concentrated, and the residue was purified by silica gel column chromatography to give 0.959 g of tho subject compound (8) in the form of a yellowish oily substance. The compound showed spectrum data which were found to be complete agreement with those of the compound as obtained in Reference Example 7.

REFERENCE EXAMPLE 14

Allyl (5R,6S)-6-[1(R)-tert-butyldimethylsilyloxyethyl]-2-[2(S)-tetrahydrofuranyl]methylpenem-3-carboxylate (15)

(3S,4R)-3-[1(R)-tert-butyldimethylsilyloxyethyl]-2-oxo-4-triphenylmethylthioazetidinone (14) (4.04 g, 8 mmole), diisopropylethylamine (4.52 g, 35 mmole), allyloxalyl chloride (5.22 g, 35 mmole), pyridine (0.64 g), silver nitrate (2.04 g), (S)-tetrahydrofuran-2-acetyl chloride (1.83 g, 12.3 mmole), xylene (35.2 mg) and triethylphosphite (7.2 ml) were treated by the same procedure as described in Reference Example 13 to give 2.46 g of the subject compound (15) in the form of a yellowish oily substance.

| Ref. Ex. No. | Comp'd. No. | Spectrum Data |
|---|---|---|
| 7 | 8 | $IR_{max}^{KBr}(cm^{-1})$: 1790(lactam C=O), 1780(ester C=O) NMR (CDCl$_3$) δ: 0.08(6H, s), 0.88(9H, s), 1.24(3H, d, J=6.6Hz, CH$_3$—C—OSi), 1.50 to 2.12(4H, m, CH$_2$—CH$_2$ in tetrahydrofuranyl), 2.90(½H, dd, J=7Hz, 15Hz, —CH$_2$—tetrahydrofuranyl), 3.01 (½H, dd, J=5Hz, 15Hz, —CH$_2$—tetrahydrofuranyl), 3.13(½H, dd, J=8Hz, 15Hz, —CH$_2$—tetrahydrofuranyl), 3.26(½H, dd, J=8Hz, 15Hz, —CH$_2$—tetrahydrofuranyl), 3.63 to 3.70 (1H, m, 6-position-H), 3.70 to 3.94(2H, m, O—CH$_2$ in tetrahydrofuranyl), 4.00 to 4.13 (1H, m, —CH—O in tetrahydrofuranyl), 4.18 to 4.29(1H, m, >CH—OSi), 4.59 to 4.77(2H, |

| Ref. Ex. No. | Comp'd. No. | Spectrum Data |
|---|---|---|
| | | m, OC$\underline{H}_2$—C≡C), 5.23 to 5.40(2H, m, C$\underline{H}$=C$\underline{H}_2$), 5.54(½H, d, J=2.0Hz, 5-position-H), 5.56(½H, d, J=2.0Hz, 5-position-$\overline{H}$), 5.95 to 6.01(1H, m, —C$\underline{H}$=CH$_2$) |
| 8 | 9 | IR$_{max}^{KBr}$(cm$^{-1}$): 1770(lactam C=O), 1700(ester C=O)<br>NMR (CDCl$_3$) δ: 0.07(6H, s), 0.88(9H, s), 1.24(3H, d, J=6Hz, C$\underline{H}_3$—$\overset{\textstyle \mid}{\text{C}}$—OSi), 1.51 to 1.68(1H, m, 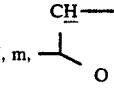), 1.79 to 2.11(3H, m, 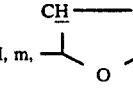), 2.90(1H, dd, J=7Hz, 15Hz, C$\underline{H}_2$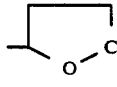), 3.66(1H, dd, J=1Hz, 5Hz, 6-position-H), 3.69 to 3.95 (2H, m, 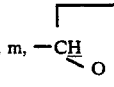), 4.00 to 4.14(1H, m, —C$\underline{H}$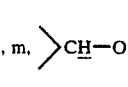), 4.14 to 4.28(1H, m, \>C$\underline{H}$—OSi), 4.58 to 4.77(2H, m, —OC$\underline{H}_2$—CH=), 5.24(1H, dd, J=1Hz, 11Hz, CH=C$\underline{H}_2$), 5.40 (1H, dd, J=1Hz, 17Hz, C$\overline{H}$=CH$_2$), 5.54(1H, d, J=1Hz, 5-position-H), 5.85 to 6.02(1H, m C$\underline{H}$=CH$_2$) |
| 9 | 10 | IR$_{max}^{KBr}$(cm$^{-1}$): 1755(lactam C=O), 1690(ester C=O)<br>NMR (CDCl$_3$) δ: 0.08(6H, s), 0.89(9H, S), 1.25(3H, d, J=6Hz, C$\underline{H}_3$CH—OSi), 1.56 to 1.71 (1H, m), 2.08 to 2.15(1H, m), 2.40 to 2.54(1H, m), 2.72 to 3.14 (2H, m, —C$\underline{H}_2$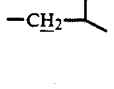), 3.39 to 3.51(1H, m), 3.66(1H, dd, J=1Hz, 5Hz, 6-position-H), 3.71 to 3.96(3H, m), 4.18 to 4.29(1H, m, \>C$\underline{H}$—OSi), 4.61 to 4.78(2H, m, OC$\underline{H}_2$CH=), 5.25(1H, dd, J=1Hz, 10Hz, CH=C$\underline{H}_2$), 5.40 (1H, dd, J=1H, 17Hz. C$\overline{H}$=CH$_2$), 5.56(1H, s, 5-position-H), 5.86 to 6.14(1H, m, C$\underline{H}$=CH$_2$) |
| 10 | 11 | IR$_{max}^{KBr}$(cm$^{-1}$): 1788(lactam C=O), 1708(ester C=O)<br>NMR (CDCl$_3$) δ: 0.07(6H, s,), 0.88(9H, s), 1.23(3H, d, J=5.6Hz, C$\underline{H}_3$CH—OSi), 1.14 to 1.90(6H, m), 2.76 to 3.69(5H, m), 3.93 to 4.03(1H, m, —C$\underline{H}$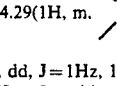), 4.18 to 4.30(1H, m, C$\underline{H}$—OSi), 4.61 to 4.87(2H, m, OC$\underline{H}_2$—CH=), 5.20 to 5.48 (2H, m, CH=C$\underline{H}_2$), 5.51(½H, d, 5-position-H), 5.58(½H, d, 5-position-H), 5.85 to 6.13(1H, m, C$\underline{H}$=CH$_2$) |
| 11 | 12 | IR$_{max}^{KBr}$(cm$^{-1}$): 1790(lactam C=O), 1710(ester C=O)<br>NMR (CDCl$_3$) δ: 0.07(6H, s), 0.88(9H, s), 1.24(3H, d, J=6Hz, C$\underline{H}_3$—$\overset{\textstyle \mid}{\text{CH}}$—OSi), 3.09(1H, dd, J=4Hz, 15Hz, C$\underline{H}_2$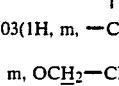), 3.88(1H, dd, J=5Hz, 15Hz, C$\underline{H}_2$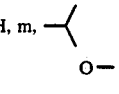), 3.67(1H. dd, J=1Hz, 5Hz, 6-position-H), 3.83 to 4.06(4H, m, 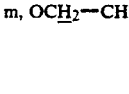), 4.18 to 4.28(1H, m, \>C$\underline{H}$—OSi), 4.61 to 4.78(2H, m, OC$\underline{H}_2$—CH=), 5.10(1H, t, J=5Hz, —C$\underline{H}$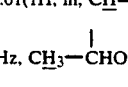), 5.23(1H, d, J=11Hz, CH=C$\underline{H}_2$), 5.39(1H, dd, J=1Hz, 17Hz, CH=C$\underline{H}_2$), 5.56(1H, d, J=2Hz, 5-positionH), 5.86 to 6.01(1H, m, C$\underline{H}$=CH$_2$) |
| 12 | 13 | IR$_{max}^{neat}$(cm$^{-1}$): 1780(lactam C=O), 1720(ester C=O)<br>NMR(CDCl$_3$) δ: 0.07(6H, s), 0.97(9H, s), 1.33(3H, d, J=6.6Hz, C$\underline{H}_3$—$\overset{\textstyle \mid}{\text{CHOSi}}$), 2.40 to 4.06(10H, m), 4.20 to 4.29(1H, m, \>C$\underline{H}$—OSi), 4.64 to 4.87(2H, m, OC$\underline{H}_2$—CH=), 5.31 to 5.57(2H, m, CH=C$\underline{H}_2$), 5.72(½H, d, J=2.64, 5- |

| Ref. Ex. No. | Comp'd. No. | Spectrum Data |
|---|---|---|
| | | position-H), 5.68(½H, d, J=3.30, 5-position-H), 5.93 to 6.22 (1H, m, C$\underline{H}$=CH$_2$) |
| 14 | 15 | IR$_{max}^{neat}$(cm$^{-1}$): 1785(lactam C=O), 1707(ester C=O), NMR(CDCl$_3$) δ: 0.07(6H, s), 0.88(9H, s), 1.08 to 1.39(3H, m, CH$_3$—C—OSi), 1.51 to 1.68(1H, m), 1.80 to 2.14(3H, m), 3.01(1H, dd, J=5Hz, 15Hz, C$\underline{H}_2$⏋O⏌), 3.13(1H, dd, J=8Hz, 14Hz, C$\underline{H}_2$⏋O⏌), 3.66(1H, dd, J=1Hz, 5Hz, 6-position-H), 3.70 to 3.96(2H, m, ⏋O/C$\underline{H}_2$⏌), 4.00 to 4.32 (2H, m, —C$\underline{H}$⏋O⏌), 4.58 to 4.84(2H, m, OC$\underline{H}_2$CH=), 5.27 to 5.51 (2H, m, CH=C$\underline{H}_2$), 5.56(1H, d, J=1Hz, 5-position-H), 5.84 to 6.09 (1H, m, C$\underline{H}$=CH$_2$) |

EXAMPLE 1

Allyl (5R,6S)-6-[1(R) hydroxyethyl]-2-(2-tetrahydrofuranyl)methylpenem-3-carboxylate (16)

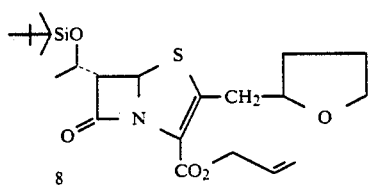

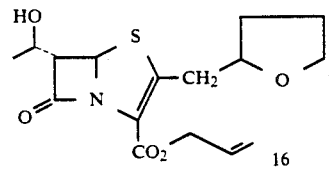

In tetrahydrofuran (0.5 ml) was dissolved allyl (5R,6S)-6-[1(R)-tert butyldimethylsilyloxyethyl]-2-(2-tetrahydrofuranyl)methylpenem-3-carboxylate (8) (249 mg, 0.55 mmole), and acetic acid (0.28 ml) and tetrabutylammonium fluoride (1.65 ml, 1.65 mmole) were added to the solution. The mixture was stirred at room temperature for 12 hours and then concentrated under reduced presure, and the resulting residue was purified by preparative thin-layer chromatography to give 177 mg (95%) of the subject compound (16) in the form of a colorless oily substance.

EXAMPLE 2

Allyl (5R,6s)-6-[1(R)-hydroxyethyl]-2-[2(R)-tetrahydrofuranyl]methylpenem-3-carboxylate (17)

Allyl (5R,6S)-6-[1(R)-tert-butyldimethylsilyloxyethyl]2-[2(R)-tetrahydrofuranyl]methylpenem-3 carboxylate (9) (238 mg, 0.52 mmole), acetic acid (0.27 ml) and tetrabutyl ammonium fluoride (1.58 ml, 1.58 mmole) were treated by the same procedure as described in Example 1 to give 312 mg (80%) of the subject compound in the form of a colorless oily substance.

EXAMPLE 3

Allyl (5R,6S)-6-[1(R)-hydroxyethyl]-2-[2(S) tetrahydrofuranyl]methylpenem-3-carboxylate (18)

Allyl (5R,6S)-6-1(R)-tert-butyldimethylsilyloxyethyl-2-[2(S)-tetrahydrofuranylmethylpenem-3 carboxylate (15) (2.27 g, 50 mmole), acetic acid (2.34 ml) and tetra butylammonium fluoride (15.2 ml, 15.2 mmole) were treated by the same procedure as described in Example 1 to give 0.677 g of the subject compound (18) in the form of a a yellowish oily substance.

EXAMPLE 4

Allyl (5R,6S)-6-[1(R)-hydroxyethyl]-2-(3-tetrahydrofuranyl)-methylpenem-3-caboxylate (19)

Allyl (5R,6S)-6-[1(R)-tert-butyldimethylsilyloxyethyl]-2-(3-tetrahydrofuranyl)methylpenem-3-carboxylate (10) (270 mg, 0.60 mmole), acetic acid (0.31 ml) and tetrabutylammonium fluoride (1.79 ml, 1.79 mmole) were treated by the same procedure as described in Example 1 to give 137 mg (68%) of the subject compound (19) in the form of a colorless solid substance.

EXAMPLE 5

Allyl (5R,6S)-6-[1(R)-hydroxyethyl]-2-(2-tetrahydropyranyl)methylpenem-3-carboxylate (20)

Allyl (5R,6S)-6-[1(R)-tert-butyldimethylsilyloxyethyl]-2-(2-tetrahydropyranyl)methylpenem-3-carboxylate (11) (124 mg, 0.264 mmole), acetic acid (0.132 ml) and tetrabutylammonium fluoride (0.793 ml, 0.793 mmole) were treated by the same procedure as described in Example 1 to give 93.2 mg (100%) of the subject compound (20) in the form of a yellowish solid substance.

EXAMPLE 6

Allyl (5R,6S)-6-[1(R)-hydroxyethyl]-2-(1,3-dioxolane-2-yl)methylpenem-3-carboxylate (21)

Allyl (5R,6S)-6-[1(R)-tert-butyldimethylsilyloxyethyl]-2-(1,3-dioxolane-2-yl)methylpenem-3-carboxylate

(12) (130 mg, 0.29 mmole), acetic acid (0.143 ml) and tetrabutylammonium fluoride (0.855 ml, 0.855 mmole) were treated y the same procedure as described in Example 1 to give 66 mg (68%) of the subject compound (21) in the form of a yellowish solid substance.

(13) (86.6 mg, 0.184 mmole), acetic acid (0.09 ml) and tetrabutylammonium fluoride (0.553 ml; 0.553 mmole) were treated by the same procedure as described in Example 1 to give 65 mg (99%) of the subject compound (22) in the form of a yellowish solid substance.

EXAMPLE 7

Allyl (5R,6S)-6-[1(R)-hydroxyethyl]-2-(1,4-dioxane-2-yl)methylpenem-3-carboxylate Allyl (5R,6S)-6-[1(R)-tert-butyldimethylsilyloxyethyl]-2-(1,4-dioxane-2-yl)methylpenem-3-carboxylate

| Example No. | Comp'd. No. | Spectrum Data |
|---|---|---|
| 1 | 16 | IR$_{max}^{neat}$ (cm$^{-1}$): 3486(OH), 1784(lactam C=O), 1708(ester C=O) |
| | | NMR(CDCl$_3$) δ: 1.35(3H, d, J=6.6Hz, CH$_3$—CH—O), 1.56 to 2.26(4H, m, 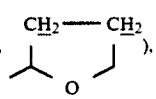), 2.88 to 3.29(2H, m, CH$_2$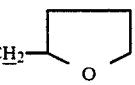), 3.67 to 3.82(2H, m), 3.82 to 3.93 (1H, m), 4.01 to 4.17(1H, m, —CH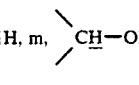), 4.17 to 4.31(1H, m, >CH—OH), 4.66 and 4.77(1H, dd, J=5Hz, 13Hz, OCH$_2$CH=, respectively), 5.26 (1H, d, J=11Hz, CH=CH$_2$), 5.40(1H, d, J=17Hz, CH=CH$_2$), 5.58(1H, d, J=3Hz, 5-position-H), 5.87 to 6.03(1H, m, CH=CH$_2$) |
| 2 | 17 | IR$_{max}^{neat}$ (cm$^{-1}$): 3450(OH), 1790(lactam C=O), 1715(ester C=O) |
| | | NMR(CDCl$_3$) δ: 1.35(3H, d, J=6Hz, CH$_3$—CH—O), 1.47 to 1.68(1H, m), 1.76 to 2.10 (3H, m), 2.94(1H, dd, J=7Hz, 15Hz, CH$_2$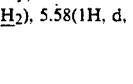), 3.24(1H, dd, J=5Hz, 15Hz, CH$_2$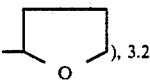), 3.64 to 3.82(2H, m), 3.82 to 3.94(1H, m), 4.01 to 4.15 (1H, m, —CH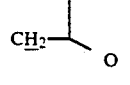), 4.15 to 4.31(1H, m, >CH—OH), 4.66 and 4.77(1H, dd, J=5Hz, 14Hz, OCH$_2$CH=, respectively), 5.26(1H, d, J=11Hz, CH=CH$_2$), 5.41(1H, d, J=17Hz, CH=CH$_2$), 5.58(1H, d, J=1Hz, 5-position-H), 5.87 to 6.04(1H, m, CH=CH$_2$) |
| 3 | 18 | IR$_{max}^{neat}$ (cm$^{-1}$): 3425(OH), 1780(lactam C=O), 1705(ester C=O) |
| | | NMR(CDCl$_3$) δ: 1.35(3H, d, J=7Hz, CH$_3$—CH—O), 1.50 to 1.67(1H, m), 1.78 to 2.12 (3H, m), 3.01(1H, dd, J=5Hz, 15Hz, CH$_2$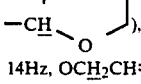), 3.13(1H, dd, J=7Hz, 15Hz CH$_2$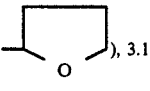), 3.68 to 3.95(3H, m), 4.01 to 4.31(2H, m), 4.66, 4.77 (1H, dd, J=5Hz, 14Hz, OCH$_2$—CH=, respectively), 5.25(1H, d, J=10Hz, CH=CH$_2$), 5.41(1H, dd, J=1Hz, 17Hz, CH=CH$_2$), 5.59(1H, d, J=1Hz, 5-position-H), 5.88 to 6.04(1H, m, CH=CH$_2$ |
| 4 | 19 | IR$_{max}^{KBr}$ (cm$^{-1}$): 3420( )H, 1770(lactam C=O), 1700(ester C=O) |
| | | NMR(CDCl$_3$) δ: 1.36(3H, d, J=6Hz, CH$_3$CH—O), 1.54 to 1.72(1H, m), 1.97 to 2.15 (1H, m), 2.39 to 2.56(1H, m), 2.76 to 3.00(2H, m, CH$_2$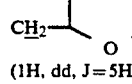), 3.40 to 3.51(1H, m), 3.71(1H, dd, J=1Hz, 7Hz, 6-position-H), 3.74 to 3.94 |

-continued

| Example No. | Comp'd. No. | Spectrum Data |
|---|---|---|
| 5 | 20 | (3H, m), 4.18 to 4.30(1H, m, \CH—OH), 4.66 and 4.77(1H, dd, J=5Hz, 14Hz, OCH₂CH=, respectively), 5.27(1H, d, J=11Hz, CH=CH₂), 5.41(1H, d, J=17Hz, CH=CH₂), 5.60(1H, d, 5-position-H), 5.87 to 6.04(1H, m, CH=CH₂) |
|  |  | IR$_{max}^{neat}$ (cm⁻¹): 3370(OH), 1780(lactam C=O), 1703(ester C=O) |
|  |  | NMR(CDCl₃) δ: 1.11 to 1.93(6H, m, —⟨tetrahydropyran⟩—), 1.34(3H, d, J=5.94Hz, CH₃CH—OH), 2.77 to 3.74(5H, m), 3.91 to 4.04(1H, m, —⟨tetrahydropyran⟩—), 4.17 to 4.30(1H, m, \CH—OH), 4.61 to 4.87(2H, m, OCH₂CH=), 5.20 to 5.47(2H, m, CH=CH₂), 5.55(½H, d, 5-position-H), 5.58(½H, d, 5-position-H), 5.86 to 6.03(1H, m, CH=CH₂) |
| 6 | 21 | IR$_{max}^{neat}$ (cm⁻¹): 3425(OH), 1785(lactam C=O), 1710(ester C=O) |
|  |  | NMR(CDCl₃) δ: 1.35(3H, d, J=7Hz, CH₃CH—O), 3.12(1H, dd, J=4Hz, 15Hz, CH₂—⟨dioxolane⟩), 3.36(1H, dd, J=5Hz, 15Hz, CH₂—⟨dioxolane⟩), 3.72(1H, dd, J=1Hz, 7Hz, 6-position-H), 3.82 to 4.05(4H, m, —⟨O—CH₂/O—CH₂⟩), 4.18 to 4.30(1H, m, \CH—OH), 4.67 and 4.78 (1H, dd, J=5Hz, 14Hz, OCH₂—CH=, respectively), 5.10(1H, t, J=5Hz, —⟨O/H/O⟩), 5.26(1H, d, J=11Hz, CH=CH₂), 5.41(1H, d, J=17Hz, CH=CH₂), 5.60(1H, d, J=1Hz, 5-position-H), 5.89 to 6.04(1H, m, CH=CH₂) |
| 7 | 22 | IR$_{max}^{neat}$ (cm⁻¹): 3300(OH), 1785(lactam C=O), 1708(ester C=O) |
|  |  | NMR(CDCl₃) δ: 1.35(3H, d, J=6.6Hz, CH₃—CH—O), 2.72 to 3.39(2H, m, CH₂—⟨O⟩), 3.58 to 3.83(8H, m), 4.17 to 4.30(1H, m, \CH—O—), 4.62 to 4.84(2H, m, OCH₂—CH=), |
|  |  | NMR(CDCl₃): 5.25 to 5.45(2H, m, CH=CH₂), 5.57(½H, d, J=2.0Hz, 5-position-H), 5.61(½H, d, J=1.3Hz, 5-position-H), 5.86 to 6.03(1H, m, CH=CH₂) |

EXAMPLE 8

Potassium (5R,6S)-6-[1(R)-hydroxyethyl]-2-(2-tetrahydrofuranyl)-methylpenem-3-carboxylate (23)

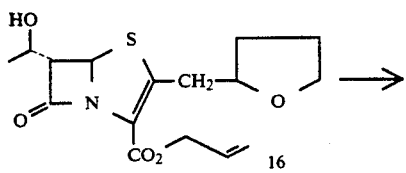

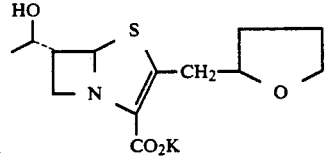

(23)

In tetrahydrofuran (5 ml) was dissolved ally (5R,6S)-6-[1(R)-hydroxyethyl]-2-(2-tetrahydrofuranyl)methyl-penem-3-carboxylate (16) (140 mg, 0.41 mmole), and tetrakistriphenylphosphine palladium (9 mg) and tri-n-butyltin hydride (0.13 ml) were added to the solution under stirring at −10° C. After stirring for 25 minutes at the same temperature, 15 the mixture was admixed with acetic acid (27 μl), followed by stirring for further 10 minutes. The mixture was concentrated, and the concentrate was admixed with water 1.8 ml) and ethyl acetate (1.2 ml), followed by addition of 2M potassium hydrogen-carbonate to adjust to a pH of 8.1. The aqueous layer was separated and concentrated through lyophilization, and the resulting solid residue was purified by column chromatography on XAD 2 to give 50 mg (36%) of the subject compound in the form of a yellowish powdered substance. Its spectrum data were found to be in complete agreement with those of the compound 24.

EXAMPLE 9

Sodium (5R,6S)-6-[1(R)-hydroxyethyl]-2-(2-tetrahydrofuranyl)-methylpenam-3-carboxylate (24)

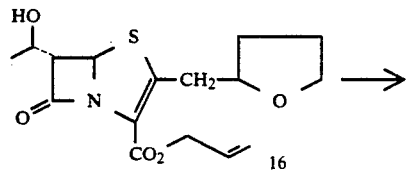

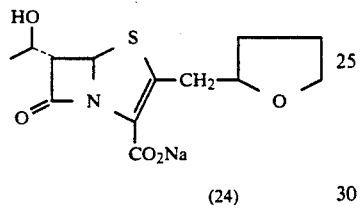

(24)

A mixture of allyl (5R,6S)-6-[1(R)-hydroxyethyl]-2-(2-tetrahydrofuranyl)methylpenem-3-carboxylate (16) (138 mg, 0.41 mmole) with sodium 2-ethylhexanoate (68 mg), tetrakis(triphenylphosphine)palladium (6.2 mg), tripheynylphosphine (6.2 mg) and ethyl acetate (0.41 ml) was stirred at room temperature for 2 hours and concentrated, and the resulting residue was purified by ODS column chromatography to give 45 mg (34%) of the subject compound (24) as a colorless powder.

$[\alpha]_D^{28°}$ $C.112°$ (c=0.345, H$_2$).

EXAMPLE 10

Sodium (5R,6S)-6-[1(R)-hydroxyethyl]-2-[2(R)-tetrahydrofuranyl]methylpenem-3-carboxylate (25)

Allyl (5R,6S)-6-[1(R)-hydroxyethyl-2 [(R)-tetrahydrofuranyl]methylpenem-3-carboxylate (17) (260 mg, 0.77 mmole), sodium 2-ethylhexanoate (128 mg), tetrakis(triphenylphosphine)palladium (112 mg), triphenylphosphine (112 mg) and ethyl acetate (0.8 ml) were treated by the same procedure as described in Example 9 to give 38 mg (15%) of the subject compound (25) as a white powder.

$[\alpha]_D^{28°}$ $C.+164°$ (c+0.192, H$_2$O).

EXAMPLE 11

Sodium (5R,6S)-6-[1(R)-hydroxyethyl]-2-(2(S)-tetrahydrofuranyl]methylpenem-3 carboxylate (26).

Allyl (5R,6S) 6-[1(R)-hydroxyethyl]-2-[1(S)-tetrahydrofuranyl]methylpenem-3-carboxylate (18) (509 mg, 1.5 mmole), sodium 2-ethylhexanoate (263 mg), tetrakis(triphenylphosphine)palladium (38 mg), triphenylphosphine (38 mg) and ethyl acetate (1.5 ml) were treated by the same procedure as described in Example 9 to give 209 mg (43%) of the subject compound (26) as a white powder.

$[\alpha]_D^{28°}$ $C.121°$ (c=0.377, H$_2$O).

EXAMPLE 12

Sodium (5R,6S)-6 1(R)-hydroxyethyl]-2-(3-tetrahydrofuranyl)methylpenem-3-carboxylate (27)

Allyl (5R,6S)-6-[1(R)-hydroxyethyl]-2-(3 tetrahydrofuranyl)methylpenem-3 carboxylate (19) (115 mg, 0.34 mmole), sodium 2-ethylhexanoate (57 mg), tetrakis(triphenylphosphine)palladium (48 mg), triphenylphosphine (48 mg) and ethyl acetate (0.35 ml) were treated by the same procedure as described in Example 9 to give 33 mg (30%) of the subject compound (27) as a white powder.

$[\alpha]_D^{28°}$ $C.121°$ (c=0.269, H$_2$O).

EXAMPLE 13

Sodium (5R,6S)-6-[1(R)-hydroxyethyl]-2-(2-tetrahydropyranyl)methylpenem-3-carboxylate (28)

Allyl (5R,6S)-6-[1(R)-hydroxyethyl]-2-(tetrahydropyranyl)methylpenem-3-carboxylate (23) (33.3 mg, 0.1 mmole), sodium 2-ethylhexanoate (16 mg), tetrakis(triphenylphosphine)palladium (3 mg), triphenylphosphine (3 mg) and ethyl acetate (3 ml) were treated by the same procedure as described in Example 9 to give 11.4 mg (38%) of the subject compound (28) as a white powder.

EXAMPLE 14

Sodium (5R,6S)-6-[1(R)-hydroxyethyl]2-(1,3-dioxolane-2-yl)methylpenem-3-carboxylate (29)

Allyl (5R,6S)-6-[1(R)-hydroxyethyl]-2-(1,3-dioxolane-2-yl)methylpenem-3-carboxylate (21) (58 mg, 0.17 mmole), sodium 2-ethylhexanoate (30 mg), tetrakis(triphenylphosphine)palladium (7.8 mg), triphenylphosphine (7.8 mg) and ethyl acetate (0.17 ml) were treated by the same procedure as described in Example 9 to give 10 mg (18%) of the subject compound (29) as a brownish solid substance.

EXAMPLE 15

Sodium (5R,6S)-6-[1(R)-hydroxyethyl]-2-(1,4-dioxane-2-yl)methylpenem 3-carboxylate (30)

Allyl (5R,6S)-6 -[1(R)-hydroxyethyl]-2-(1,4-dioxane-2-yl)methylpenem-3-carboxylate (11.5 mg, 0.03 mmole), sodium 2-ethylhexanoate (55 mg), tetrakis(triphenylphosphine)palladium (1 mg), triphenylphosphine (1 mg) and ethyl acetate (1 ml) were treated by the same procedure as described in Example 9 to give 3.3 mg (33%) of the subject compound (30) as a white powder.

| Example No. | Comp'd. No. | Spectrum Data |
|---|---|---|
| 9 | 24 | $IR_{max}^{KBr}$(cm$^{-1}$): 3350(OH), 1760(lactam C=O) |

-continued

| Example No. | Comp'd. No. | Spectrum Data |
|---|---|---|
| | | NMR (D$_2$O) δ: 1.18(3H, d, J=7Hz, C$\underline{H}_3$—CH—O), 1.42 to 1.62(1H, m), 1.68 to 2.03(3H, m), 2.62 to 3.15(2H, m, C$\underline{H}_2$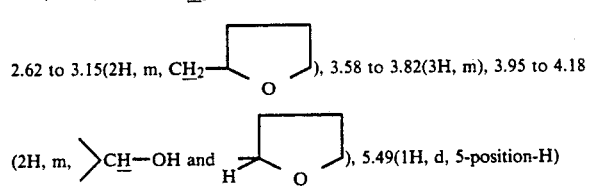), 3.58 to 3.82(3H, m), 3.95 to 4.18 (2H, m, >C$\underline{H}$—OH and 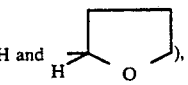), 5.49(1H, d, 5-position-H) |
| 10 | 25 | IR$_{max}^{KBr}$(cm$^{-1}$): 3375(OH), 1760(lactam C=O) <br> NMR (D$_2$O) δ: 1.16(3H, d, J=6Hz, C$\underline{H}_3$—CH—O), 1.38 to 1.58(1H, m), 1.65 to 2.00(3H, m, 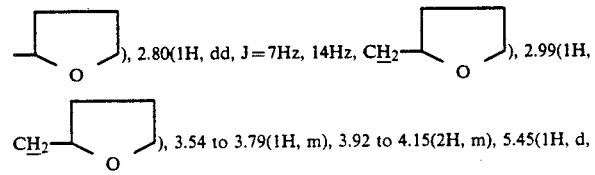), 2.80(1H, dd, J=7Hz, 14Hz, C$\underline{H}_2$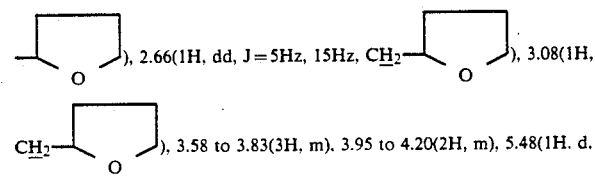), 2.99(1H, dd, J=6Hz, 15Hz, C$\underline{H}_2$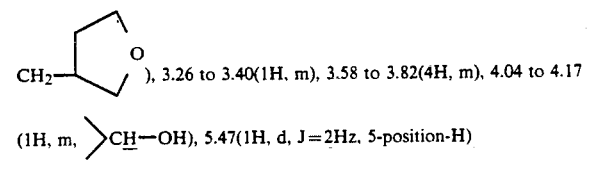), 3.54 to 3.79(1H, m), 3.92 to 4.15(2H, m), 5.45(1H, d, 5-position-H) |
| 11 | 26 | IR$_{max}^{KBr}$(cm$^{-1}$): 3375(OH), 1760(lactam O=O) <br> NMR (D$_2$O) δ: 1.17(3H, d, J=7Hz, C$\underline{H}_3$—CH—O), 1.44 to 1.63(1H, m), 1.63 to 2.03(3H, m, 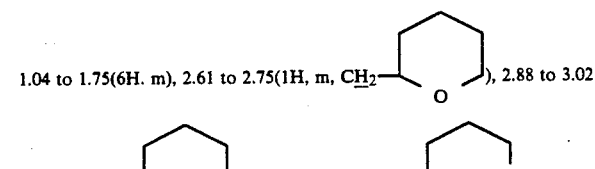), 2.66(1H, dd, J=5Hz, 15Hz, C$\underline{H}_2$ ), 3.08(1H, dd, J=8Hz, 15Hz, C$\underline{H}_2$ ), 3.58 to 3.83(3H, m), 3.95 to 4.20(2H, m), 5.48(1H, d, J=5-position-H) |
| 12 | 27 | IR$_{max}^{KBr}$(cm$^{-1}$): 3400(OH), 1755(lactam C=O) <br> NMR (D$_2$O) δ: 1.16, 1.17(3/2H, d, J=6Hz, C$\underline{H}_3$—CH—O, respectively), 1.41 to 1.62(1H, m), 1.88 to 2.04(1H, m), 2.28 to 2.46(1H, m), 2.46 to 3.00(2H, m, C$\underline{H}_2$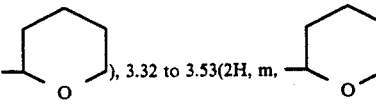), 3.26 to 3.40(1H, m), 3.58 to 3.82(4H, m), 4.04 to 4.17 (1H, m, >C$\underline{H}$—OH), 5.47(1H, d, J=2Hz, 5-position-H) |
| 13 | 28 | IR$_{max}^{KBr}$(cm$^{-1}$): 3340(OH), 1740(lactam C=O) <br> NMR (D$_2$O) δ: 1.15(3/2H, d, J=2Hz, C$\underline{H}_3$—CH—OH), 1.17(3/2H, d, J=1.4Hz, C$\underline{H}_3$CH—OH), 1.04 to 1.75(6H, m), 2.61 to 2.75(1H, m, C$\underline{H}_2$ ), 2.88 to 3.02 (1H, m, C$\underline{H}_2$ ), 3.32 to 3.53(2H, m, 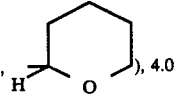), 3.68 to 3.72(1H, m, 6-position-H), 3.78 to 3.83(1H, m, ), 4.05 to 4.14(1H, m, >C$\underline{H}$—OH), 5.45(1H, d, 5-position-H) |
| 14 | 29 | IR$_{max}^{KBr}$(cm$^{-1}$): 3400(OH), 1765(lactam C=O) |

| Example No. | Comp'd. No. | Spectrum Data |
|---|---|---|
| | | NMR (D₂O) δ: 1.17(3H, d, J=6Hz, C$\underline{H}_3$—CHOH), 2.94(1H, dd, J=5Hz, 15Hz, C$\underline{H}_2$—⟨O-CH₂CH₂-O⟩), 3.21 1H, dd, J=5Hz, 15Hz, C$\underline{H}_2$—⟨O⟩), 3.73(1H, dd, J=1Hz, 5Hz, 6-position-H), 3.75 to 3.99(4H, m, —⟨O—CH₂ / O—CH₂⟩), 4.03 to 4.15(1H, m, \C$\underline{H}$—OH), 5.03(1H, t, J=5Hz, H—⟨O⟩), 5.48(1H, d, 5-position-H) |
| 15 | 30 | IR$_{max}^{KBr}$(cm⁻¹): 3440(OH), 1755(lactam C=O) NMR (D₂O) δ: 1.16(3H, d, J=4.6Hz, C$\underline{H}_3$—CH—OH), 2.63 to 2.77(1H, m, C$\underline{H}_2$—⟨O⟩), 2.94 to to 3.04(1H, m, C$\underline{H}_2$—⟨O⟩), 3.20 to 3.86(8H, m), 4.08 to 4.12(1H, m, \C$\underline{H}$—OH), 5.48(1H, d, 5-position-H) |

REFERENCE EXAMPLE 15

(3S,4R)-3-[1(R)-Tert-butyldimethylsilyloxyethyl]-2-oxo-4-[(3-tetrahydrofuranyl)methylcarbonylthio]azetidine (33)

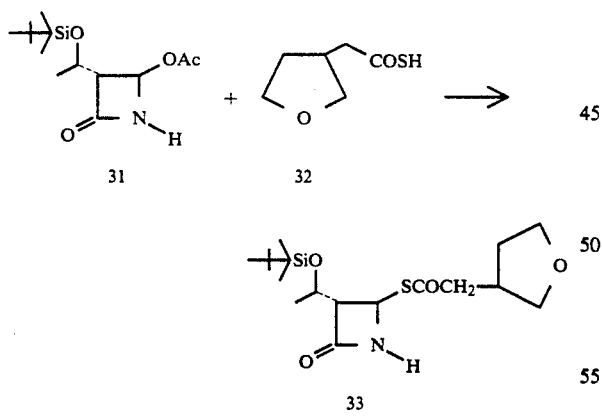

In tetrahydrofuran (730 ml) was dissolved (3R,4S)-4-acetoxy-3-[1(R)-tert-butyldimethylsilyloxyethyl]-2-oxoazetidine (31) (25.2 g, 90 mmole), and water (438 ml) and tetrahydrofuran-3-thioacetic acid (32) (15.4 g, 105 mmole) were added successively to the solution under stirring, followed by adding dropwise 1N NaOH to adjust to pH 7.6 and stirring overnight at room temperature. Ethyl acetate was added to the mixture, which was washed with water and then dried over anhydrous magnesium sulfate. The solvent was removed under reduced pressure, and the residue was purified by column chromatography to give 27.6 g (82%) of the subject compound (33) in the form of a colorless crystalline substance.

IR$_{max}^{KBr}$(cm¹): 1770(lactam c=0), 1695(ester c=0).
NMR(CDCl₃) δ: 0.077(3H,s), 0.085(3H,s), 0.88(9H,s), 1.21 (3H,d,J=6 Hz, $$CH_3—\underset{\underset{OSi)}{|}}{C}—$$

1.50 to 1.65(1H,m), 2.06 to 2.20(1H,m), 2.57 to 2.76(3H,m), 3.16(1H,dd,J=3 Hz,4 Hz,3-position-H), 3.39 to 3.46(1H,m), 3.70 to 3.96(3H,m), 4.20 to 4.31 1H,m>CH—OSi), 5.31(0.5H,d,J=1.3 Hz,4-position-H), 5.32(0.5H,d,J=2.6 Hz,4-position-H), 6.30(1H,br.s.,NH).

REFERENCE EXAMPLE 16

Trichloroethyl (5R,6S)-6-[1(R)-tert-butyldimethylsilyloxyethyl]-2-(3-tetrahydrofuranyl)methylpenem-3-carboxylate (34)

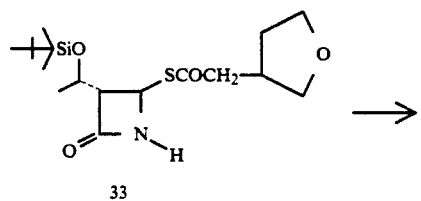

-continued

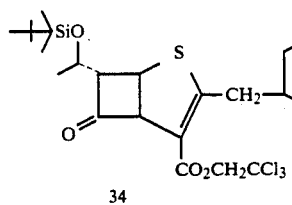

In xylene (10 ml) was dissolved a mixture of (3S,4R)-3-[1(R)-tert-butyldimethylsilyloxyethyl]-2-oxo-4-[(3-tetrahydrofuranyl)methylcarbonylthio]azetidine (33) (1.87 g, 5 mmole) and 2,6-lutidine (0.804 g, 7.5 mmole), and a solution of oxalyl chloride (0.952 g, 7.5 mmole) in xylene (5 ml) was added dropwise to the solution under stirring at 0° C. After stirring for 20 minutes, the solution was admixed with a mixture of α,α,α-trichloroethanol (1.49 g, 10 mmole), pyridine (0.59 g, 7.5 mmole) and xylene (10 ml) at 0° C. to allow the reaction to proceed for 1 hour.

The salt which crystallized out was filtered out, and the filtrate was washed with water and dried over anhydrous sodium sulfate. The drying agent was filtered out, and the filtrate was admixed with triethylphosphite (4 ml), followed by heating under reflux at 140° C. for 23 hours. The solvent was removed under reduced pressure, and the residue was purified by column chromatography to give 0.602 g (22%) of the subject compound (34) in the form of a yellowish solid substance.

IR$_{max}^{neat}$(max): 1790(lactam C=O), 1730(ester C=O).
NMR(CDCl$_3$): 0.08(6H,s), 0.89(9H,s), 1.25(3Hd,J=7 Hz,

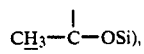

1.47 to 1.74(1H,m), 2.02 to 2.17(1H,m), 2.42 to 2.56(1H, m,

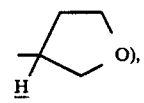

2.76 to

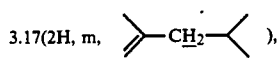

3.40 to 3.50 (1H,m), 3.70(1H,dd,J=2 Hz,4 Hz,6-position-H), 3.67 to 3.96(3H,m), 4.18 to 4.30(1H,m,>CH—OSi), 4.85(2H,s,—CH$_2$CCl$_3$), 5.60(1H,d,5-position-H).

EXAMPLE 16

Trichloroethyl (5R,6S)-6-[1(R)-hydroxyethyl]-2-(3-tetrahydrofuranyl)-methylpenem-3-carboxylate (35)

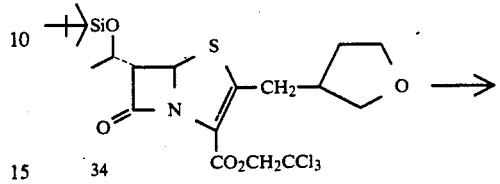

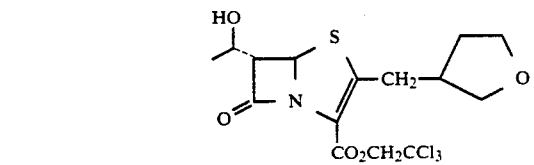

In tetrahydrofuran (6 ml) was dissolved trichloroethyl (5R,6S)-6-[1(R)-tert-butyldimethylsilyloxyethyl]-2-(3-tetrahydrofuranyl)methylpenem-3-carboxylate (34), (3.74 g, 6.87 mmole), and acetic acid (3.25 ml) and n-tetrabutylammonium fluoride (1M solution in tetrahydrofuran) (20.6 ml) were added successively to the solution, followed by stirring overnight at room temperature.

The mixture was diluted with ethyl acetate, and the solution was washed with saturated aqueous sodium hydrogen-carbonate solution, saturated aqueous potassium hydrogen-carbonate solution and brine, successively, and dried over anhydrous sodium sulfate. The solvent was removed under reduced pressure, and the residue was purified by column chromatography to give 1.813 g (58%) of the subject compound (35) in the form of a yellowish amorphous substance.

IR$_{max}^{neat}$(cm$^{-1}$): 3375(OH), 1790(lactam C=O), 1725(ester C=O).
NMR(CDCl$_3$) δ:

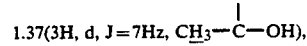

1.50 to 1.72 (1H,m), 1.90 to 2.08 (2H,m), 2.40 to 2.58

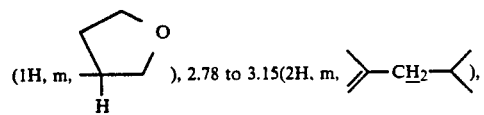

3.39 to 3.50(1H,m), 3.65 to 3.96(4H,m), 4.15 to 4.33(1H,m,>CH—OH), 4.83(1H,dd,J=2 Hz,12 Hz,CH$_2$CCl$_3$), 4.91(1H,dd,J=4 Hz,12 Hz, CH$_2$CCl$_3$), 5.62(1H,d,J=2 Hz,5-position-H)

EXAMPLE 17

(5R,6S)-6-[1(R)-Hydroxyethyl]-2-(3-tetrahydrofuranyl)methylpenem-3-carboxylic acid (36)

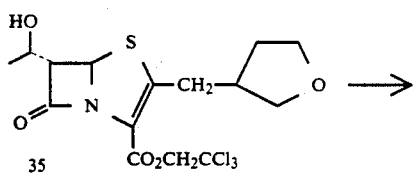

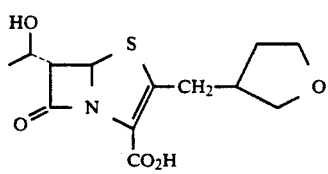

In tetrahydrofuran (16.3 ml) was dissolved trichloroethyl (5R,6S)-6-[1(R)-hydroxyethyl]-2-(3-tetrahydrofuranyl)methylpenem-3-carboxylate (35)(1.63 g, 3.55 mmole), and 1M potassium dihydrogenphosphate (32.6 ml) and zinc (3.26 g) were added to the solution, followed by stirring at room temperature for 4 hours. The insoluble matter was filtered out, and the filtrate was extracted with ethyl acetate The ethyl acetate layer was washed with water and dried over anhydrous magnesium sulfate, and the solvent was removed under reduced pressure. The residue was recrystallized from ethyl acetate to give 0.856 g (80%) of the subject compound (36) in the form of colorless crystals.

$IR_{max}^{neat}(cm^{-1})$: 3350(OH), 1780(lactam C=O), 1700(carboxylic acid).

$NMR(CDCl_3)$ δ:

1.28(3H, d, J=1Hz, $C\underline{H}_3$—C—OH), 1.51 to 1.72 (1H,m), 1.93 to 2.12(2H,m), 2.36 to 2.51

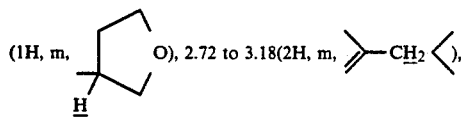

(1H, m, O), 2.72 to 3.18(2H, m, $\rangle$—CH$_2$$\langle$), 3.31 to 3.44(1H,m), 3.60 to 3.87(4H,m), 4.06 to 4.18(1H,m), 5.67(1H,5-position-H).

m.p. : 133° to 134° C.

$[\alpha]_D^{28°}$ $C$:+328° (c=0.155, acetone).

Therapeutic effect on the experimental infection in mice

Among the novel compounds as obtained according to the present ivention, the compound (27) was used to carry out a therapy experiment with infected animals. With male mice of ICR strain (5-weeks aged, weighing from 23 to 27 g) being employed as an experimental animal, E. coli KC-14 was inoculate intraperitoneally to the mice, and, 2 hours later, the compound (27) was administered subcutaneously or orally. The mice were observed for survival or death 5 days later to compare the therapeutic effect, wherein the compound (39) was used as a control reference. The results are shown in Table 5.

TABLE 5

| Test microbe | Amount of microbial cells inoculated | Route of administ'n | $ED_{50}$ (mg/kg) Comp'd (27) | Comp'd. (39) |
|---|---|---|---|---|
| E. coli KC-14 | 4.8 × 10$^5$ (colony forming unit) | Subcut. Oral | 3.0 9.5 | 3.9 15.1 |
| S. aureus Smith | 3.8 × 10$^6$ (colony forming unit) | Subcut. | 1.11 | 1.0 to 2.0 |

Acute toxicity test

Among the novel compounds as obtained according to the present invention, the compound (27) was selected to conduct an acute toxicity test. Mice of ICR strain (4-weeks aged), being used as an experimental animal, were given the compound through oral and intravenous routes.

In the case of intravenous administration, all mice of the male and female groups having received 3 g/kg of the compound (27) were all found to survive, while mice of the male and female groups given orally 5 g/kg were all found to survive.

Measurement of the minimum inhibition concentration

The novel compounds according to the present invention and the compound as obtained in Reference Example were subjected to determination of minimum inhibition concentration (MIC) by means of the agar plate dilution method in accordance with the MIC Measurement Standard Method specified by Chemotherapy Society of Japan. The inoculation amount of each microbe was 10$^6$ colony forming unit. The minimum concentration to inhibit growth of the test microbes after incubation at 37° C. for 18 hours was tabled as g/ml. The results are shown in the following Table.

| Test microbe | Compound No. | | | | | | | | |
|---|---|---|---|---|---|---|---|---|---|
| | 24 | 25 | 26 | 27 | 28 | 29 | 30 | 37 | 38 |
| S. aureus FDA 209P JC-1 | 0.05 | 0.05 | <0.025 | <0.025 | 0.1 | 0.2 | 0.2 | 0.39 | 0.2 |
| M. lutues ATCC 9341 | 0.25 | 0.2 | 0.1 | <0.025 | 0.2 | 0.2 | 0.2 | 0.2 | 0.2 |
| E. coli NIHJ JC-2 | 1.56 | 0.78 | 6.25 | 0.79 | | 3.13 | 12.5 | 25 | 12.5 |
| K. pneumoniae PCI 602 | 0.78 | 0.39 | 0.78 | 0.1 | 0.39 | 1.56 | 1.56 | 3.13 | 3.13 |
| Ser. marcescens-IAM 1136 | 12.5 | 6.25 | | 1.56 | | 6.25 | 12.5 | 25 | 25 |
| Pr. morganii IFO 3848 | 0.78 | 0.39 | 3.13 | 0.39 | 3.13 | 6.25 | 3.13 | 12.5 | 12.5 |

-continued

| Test microbe | Compound No. | | | | | | | | |
|---|---|---|---|---|---|---|---|---|---|
| | 24 | 25 | 26 | 27 | 28 | 29 | 30 | 37 | 38 |
| Ent. cloacae 963 | 0.39 | 0.2 | 1.56 | 0.2 | 3.13 | 1.56 | 1.56 | 25 | 25 |
| Al. fecalis IFO 13111 | 0.78 | 0.78 | 0.78 | 0.39 | 1.56 | 0.78 | 1.56 | 6.25 | 12.5 |
| E. coli W3630/Rms 212 | 3.13 | 0.78 | 6.25 | 0.78 | | 3.13 | 12.5 | 25 | 25 |
| E. coli W3630/Rms 213 | 1.56 | 0.78 | 12.5 | 0.78 | | 3.13 | 6.25 | 25 | 25 |
| Pr. vulgaris Gn 7919 | 3.13 | 1.56 | 3.13 | 0.78 | 12.5 | 3.13 | 6.25 | 3.13 | 3.13 |
| B. frangilis GM 7000 | 0.05 | 0.05 | <0.025 | 0.05 | 0.2 | 0.05 | 0.2 | 0.39 | 0.78 |
| B. frangilis V-280-1 | 0.05 | 0.05 | 0.1 | 0.05 | 0.2 | 1.56 | 0.2 | 6.25 | 12.5 |
| F. varium ATCC 8501 | 0.1 | 0.2 | 0.39 | 0.1 | 0.39 | 0.39 | 0.78 | 6.25 | 6.25 |

As a control, the compounds 37, 38 and 39 were found to show their antimicrobial activities as given in the above Table.

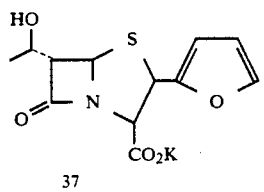

37

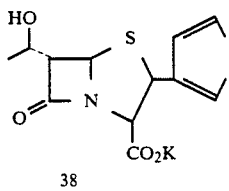

38

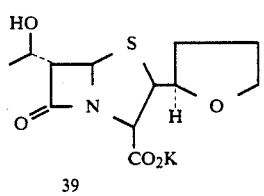

39

REFERENCE EXAMPLE 17

(Stability test against renal dehydropeptidase)

Method: 0.325 μ/ml (final concentration) of purified human renal dehydropeptidase and 100 μM (final concentration) of each test compound were heated to 37° C. in 50 mM of Tris/HCl buffer (pH 7.0) and samples were collected at planned hours. Remaining amounts of the compound in the samples were analyzed quantitatively and the half-life period of each compound was calculated.

| Test compound | Result: | |
|---|---|---|
| | Half-life ($t_1/2$ hr) | Remaining amount after 9 hours (μg/ml) |
| Imipenem | 3.02 | 14.7 |
| Sch 29482 | 1.44 | 4.9 |
| Compound 27 | 3.81 | 70.8 |

As shown in the table, Compound 27 is more stable than Sch 29482 and Imipenem. Compound 27 exhibits remarkable difference from Sch 29482 and Imipenem in the remaining amount after 9 hours.

We claim:

1. A penem derivative represented by the formula,

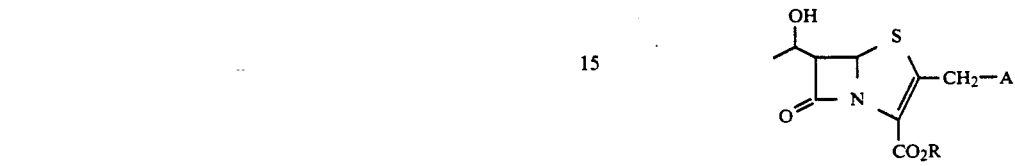

wherein R denotes hydrogen atom or allyl group, and A denotes an aliphatic 5- or 6-membered heterocyclic group having one or two oxygen atoms in the ring, or a pharmaceutically acceptable salt thereof.

2. A compound according to claim 1, wherein the group A is terahydrofuryl group.

3. A compound according to claim 1, wherein the group A is tetrahydropyranyl group.

4. A compound according to claim 1, wherein the group A is 1,3-dioxolanyl group.

5. A compound according to claim 1, wherein the group A is 1,4-dioxolanyl group.

6. A compound according to claim 1 wherein R is allyl group.

7. A compound according to claim 1, wherein the salt is sodium, potassium or calcium salt.

8. A compound according to claim 1, wherein the compound is an optically active compound.

9. A compound according to claim 1, wherein the carbon atom at the base of the hydroxyl group in the hydroxyethyl group which is attached to the 6-position of the penem ring has R configuration.

10. A compound according to claim 1, wherein the 5 position is R configuration and the 6-position is S configuration.

11. A pharmaceutical composition useful as an antibacterial agent and comprised of a penem compound represented by the formula

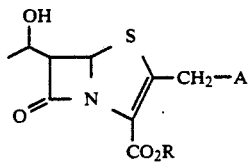

wherein R denotes hydrogen or allyl group, and A denotes an aliphatic 5- and 6-membered heterocyclic group having one or two oxygen atoms in the ring, or a pharmaceutically acceptable salt thereof, and a biologically acceptable carrier.

12. The pharmaceutical composition according to claim 11, which contains the active ingredient in a daily dose of 50 mg to 5 g.

13. A method for treating bacterial infections in a host which comprises administering to said host an antibacterial-effective amount of the pharmaceutical composition of claim 11.

* * * * *